United States Patent [19]

Raff

[11] Patent Number: 4,970,070

[45] Date of Patent: Nov. 13, 1990

[54] PROTECTIVE MONOCLONAL ANTIBODY COMPOSITIONS FOR INFECTIONS DUE TO GROUP B STREPTOCOCCUS

[75] Inventor: Howard V. Raff, Seattle, Wash.

[73] Assignee: Genetic Systems Corporation, Seattle, Wash.

[21] Appl. No.: 189,359

[22] Filed: May 2, 1988

Related U.S. Application Data

[63] Continuation-in-part of Ser. No. 944,495, Dec. 19, 1986, which is a continuation-in-part of Ser. No. 828,005, Feb. 7, 1986, abandoned.

[51] Int. Cl.$^5$ .................... A61K 39/40; C07K 15/28; C12N 5/10

[52] U.S. Cl. .................. 424/87; 424/85.8; 530/387; 530/388; 530/389; 530/808; 530/809; 435/70.21; 435/240.26; 435/240.27; 435/240.2; 435/948; 436/548; 935/100; 935/104; 935/107; 935/110

[58] Field of Search .............. 435/240.26, 240.27, 435/240.2, 68, 948, 885, 70.21; 530/387, 388, 389, 808; 424/85, 87, 85.8; 935/100, 104, 107, 110; 436/548

[56] References Cited

U.S. PATENT DOCUMENTS

| | | | |
|---|---|---|---|
| 4,464,465 | 8/1984 | Lostroum | 435/68 |
| 4,587,121 | 5/1986 | Collins et al. | 424/87 |
| 4,675,287 | 6/1987 | Reisfeld et al. | 435/7 |
| 4,677,070 | 6/1987 | Larrick et al. | 435/240 |
| 4,734,279 | 3/1988 | Stephan et al. | 424/85 |

FOREIGN PATENT DOCUMENTS 0163493 5/1985 European Pat. Off. .

OTHER PUBLICATIONS

Ruch, F. E., Jr., "Monoclonal Autibody to Streptococcal Group B Carbohydrate: Applications in Latex Agglutination and Immunoprecipitin Assays", *J. Clin Microbiol.*, 16(1): 145–152, Jul. 1982.
Shigeoka, A. O. et al. "Protective Efficacy of Hybridoma Type-Specific Antibody Against Experimental Infection with Group-B Steptococcus", *J. Inf. Dis.*, 149(3): 363–372, Mar. 1984.
Sorensen, R. U. et al., "Defective Cellular Immunity to Gram-Negative Bacteria in Cystic Fibrosis Patients", *Infection and Immunity*, 23: 398–402, Feb. 1979.
Moreno, C. et al., "Innunological Properties of Monoclonal Antibodies Specific for Meningococcal Polysaccharides: The Protective Capacity of IgM Autibodies Specific for Polysaccharide Group B", *J. Gen. Microbiol.*, 129: 2451–2456, 1983.
Hienaux, J. R. et al., "Study of the Idiotypy of Lipopoly-Saccharide-Specific Polyclonal and Monoclonal Antibodies", *Eur. J. Immunol.*, 12:797–803, 1982.
Pluschke, G. et al., "Sodium Dodecyl Sulphate-Polyacrylamide Gel Electrophoresis and Monoclonal Antibodies as Tools for the Subgrouping of *Escherichia Coli* Lipopolysaccharide 018 and 023 Antigens", *Infection and Immunity*, 51(1):286–293, Jan. 1986.
Raff, Howard V., "Human Monoclonal Antibodies to Group B Streptococcus-Reactivity and In Vivo Protection Against Multiple Serotypes", *J. Exp. Med.*, vol. 168, pp. 905–917, Sep. 1988.
Baker (1986), N. Engl. J. Med., 314:1702–1704.
Backer et al. (1976), N. Engl. J. Med., 294:753–756.
Kaijser et al. (1972), Scand. J. Immunol., 1:27–32
Kaijser et al. (1977), Infect. Immun., 17:286–289.
Egan et al. (1983), J. Exp. Med., 158:1006–1011.
Yoder et al. (1986), Pediatr. Clin. N. Amer., 33:481–501.
Lancefield et al. (1975), J. Exp. Med., 142:165–179.
Christensen et al. (1984), Eur. J. Pediatr., 142:86–88.
Gotoff et al. (1986), J. Infect. Dis., 153:511–519.
Anthony et al. (1985), J. Infect. Dis., 151:221–226.
Collins et al. (1984), Am. J. Med., 76:155.
Teng et al. (1985), Proc. Natl. Acad. Sci. USA, 82:1790.
Hornberger et al. (1985), Fed. Am. Soc. Exp. Biol. 69th Annual Meeting, Abs. No. 5366.
Cryz et al. (1984), Infect. Immun., 45:139.
Gigliotti et al. (1984), J. Infect. Dis., 149:43.
Givner et al. (1985), J. Infect. Dis., 151:217.
Ruch, Jr. et al. (1982), J. Clin. Microbiol., 16:145.
Baltimore et al. (1979), J. Infect. Dis., 140:81.
Shigeoka et al. (1984), J. Infect. Dis., 150:63–70.
Hemming et al. (1987), J. Infect. Dis., 156:655–658.
Harper et al. (1986), Rev. Infect. Dis., 8:S401–S408.

*Primary Examiner*—Margaret Moskowitz
*Assistant Examiner*—Kay E. Cheney
*Attorney, Agent, or Firm*—Townsend and Townsend

[57] ABSTRACT

Immortalized cell lines have been produced that secrete human monoclonal antibodies capable of binding to bacterial species which are a major cause of neonatal sepsis and meningitis. These antibodies have been found to be protective against lethal challenges of these bacteria, which include group B streptococcus, *E. coli*, K1, and *Neisseria meningitidis* group B. Pharmaceutical compositions containing these antibodies, which can be in combination with other monoclonal anitbodies, blood plasma fractions and antimicrobial agents, and the prophylactic and therapeutic use of such compositions in the management of infections, are included.

42 Claims, No Drawings

PROTECTIVE MONOCLONAL ANTIBODY COMPOSITIONS FOR INFECTIONS DUE TO GROUP B STREPTOCOCCUS

CROSS-REFERENCE TO RELATED APPLICATIONS

This is a continuation-in-part application of U.S. Pat. Ser. No. 944,495, filed Dec. 19, 1986, which is a continuation-in-part of U.S. Pat. Ser. No. 828,005, filed Feb. 7, 1986, which are incorporated herein by reference.

FIELD OF THE INVENTION

The present invention relates to the application of immunological techniques to provide novel materials useful in treating and diagnosing bacterial infections and, more particularly, to the production and application of human monoclonal antibodies that are capable of protecting against certain infections in human neonates.

BACKGROUND OF THE INVENTION

Gram-positive and gram-negative bacteria may cause life-threatening disease in infected patients. There is an increased incidence of such infections in prematurely born infants and patients who have serious underlying medical conditions. Newborns have an immature immune system and are acutely susceptible to sepsis and meningitis caused by certain species of gram-negative and gram-positive bacteria. Encapsulated strains of *Escherichia coli*, *Neisseria meningitidis* group B, *Hemopohilus influenzae* type B, and *Streptococcus agalactiae* (group B streptococcus) comprise the majority of isolates in neonates, although other isolates may also cause such infections. Regardless of whether the infant develops the infection at birth (early onset) or within the first weeks of life (late onset), mortality and morbidity rates remain high, despite aggressive medical intervention.

The group B streptococcus is the predominant gram-positive bacterium causing severe or life-threatening neonatal infections (Baker, 1986, *N. Engl. J. Med.* 314:1702). The group B streptococci are identified by a group-specific carbohydrate, the B polysaccharide, and may be further divided into five serotypes, Ia, Ib, Ic, II, and III based on serologically diverse capsules. Strains from the capsule types Ia, Ib, II and III are the predominant clinical isolates, any of which may cause neonatal sepsis; type III capsular strains are associated with the majority of cases of neonatal meningitis. Baker et al., 1976, *N. Engl. J. Med.* 294:753. Among gram-negative organisms causing meningitis in the neonatal population, the encapsulated *E. coli* strain K1 is the primary isolate.

Antibiotics have long been the primary therapeutic tool for the control and eradication of gram-positive and gram-negative infections. The continued incidence and severity of the infections, the continual emergence of antibiotic resistant bacterial strains, and the inherent toxicity of some antibiotics, however, illustrate the limitations of antibiotic therapy. These observations have prompted searches for other prophylactic and therapeutic approaches.

Antibodies may provide an alternative means for eliminating bacteria from an infected individual or for preventing their colonization in uninfected individuals at risk for developing disease. It is believed that antibodies which bind with antigens accessible (externally exposed) on live bacteria may facilitate bacterial destruction, which process may occur by any of several mechanisms, including (1) direct lysis of the bacteria in the presence of serum complement, (2) bacteriostasis, by the blockading of nutrient scavenger receptors, (3) opsonization and subsequent phagocytosis of the bacteria in the presence or absence of serum complement, or (4) prevention of attachment of the bacteria to host tissues (Mims, C. A., "Recovery from Infection," in *The Pathogenesis of Infectious Disease*. pp. 198–222, Mims, C. A., Ed., Academic Press (1982)). For bacteria that possess surface carbohydrate molecules, such as lipopolysaccharide (LPS) and/or capsules, antibody appears to be most effective via opsonization mechanisms (Kaijser, B., et al., "The Protective Effect Against *E. coli* of O and K Antibodies of Different Immunoglobulin Classes," *Scand. J. Immunol.* 1:276 (1972)). Therefore, antibodies directed to accessible carbohydrate structures may provide an effective regimen for therapy or prophylaxis.

In general, mammals that are exposed to disease-producing bacteria produce antibodies that are specific for LPS or capsule. These antigens, which often form the basis for serotyping the bacterial strains, are chemically diverse structures composed of frequently repeating oligosaccharide molecules. Since LPS or capsule are often the immunodominant bacterial antigens, serotype specific antibodies have been the most studied of potentially therapeutic antibodies. However, because of the strain specificity of these antibodies, and the diversity of carbohydrate antigens on pathogenic gram-positive and gram-negative bacteria, it would be extremely difficult and costly to produce a therapeutic formulation containing only serotype specific antibodies (see, e.g., Kaijser, B. and Ahlstedt, S., "Protective Capacity of Antibodies Against *Escherichia coli* O and K Antigens," *Infect. Immun.* 17:286–292 (1977); and Morrison, D. C. and Ryan, J. L., "Bacterial Endotoxins and Host Immune Response," *Adv. Immunol.* 28:293–450 (1979)). Regardless, various reports have stimulated visions that immunotherapeutic approaches could be found to treat bacterial disease.

Fractionated human plasma, enriched for immune globulins containing specific and protective antibodies against the infection organisms, have been somewhat effective against *Pseudomonas aeruginosa* infections. (Collins, M. S. and Robey, R. E., "Protective Activity of an Intravenous Immune Globulin (Human) Enriched in Antibody Against Lipopolysaccharide Antigens of *Pseudomonas aeruginosa*," *Amer. J. Med.* 3:168.174 (1984)). However, certain inherent limitations have prevented the widespread use of immune globulins in the treatment of life-threatening bacterial disease For instance, such compositions are assembled from large pools of plasma samples that have been preselected for the presence of a limited number of particular antibodies Typically, these pools consist of samples from a thousand donors who may have low titers to some pathogenic bacteria. Thus, at best, there is only a modest increase in the resultant titer of desired antibodies.

Another such limitation is that the preselection process itself requires very expensive, continuous screening of the donor population to assure product consistency. Despite considerable effort, product lots can still vary between batches and geographic regions.

Yet another such limitation inherent in immune globulin compositions is that their use results in coincident administration of large quantities of extraneous proteinaceous substances (e.g., viruses) having the potential to cause adverse biologic effects The combination of low titers of desired antibodies and high content of extraneous substances often limits, to suboptimal levels, the amount of specific and thus beneficial immune globulin(s) administrable to the patient.

In 1975, Kohler and Milstein reported that certain mouse cell lines could be fused with mouse spleen cells to create hybridomas which would secrete pure "monoclonal" antibodies (Kohler, G. and Milstein, C., "Continuous Cultures of Fused Cells Secreting Antibody of Predefined Specificity," Nature 256:495–497 (1975)). Using this technology, mouse monoclonal antibodies specific to certain capsule serotypes of group B streptococci have been reported to be protective in experimental animal models (see. e.g., Egan, M. L. et al., "Protection of Mice from Experimental Infection with Type III Group B Streptococcus Using Monoclonal Antibodies," 1983, *J. Exp. Med.*, 1:1006–1011, Shigeoka et al., 1984, *J. Inf. Dis.* 149:363; and Yoder et al., 1986, *Pediat. Clin. N. Amer.* 33:481). These studies followed earlier work which had shown that heterologous antisera possessing group B streptococcus type-specific antibody was protective in animals (e.g. Lancefield, 1972, *Streptococci and Streptococcal Disease* (Wannamaker and Matson, Eds, Academic Press, NY, p.57), and Lancefield et al., 1975, *J. Exp. Med.* 142:165).

Retrospective clinical studies comparing healthy human neonates with those infected by group B streptococci have also shown that low infection rates correlated best with elevated maternal and type-specific antibody titers, while increased rates of infection occurred among premature infants with the lowest antibody titers. Christensen et al., 1984, *Eur. J. Pediatr.* 142:86 and Gotoff et al., 1986, *J. Infect. Dis.* 153:511. Moreover, passively administered human serum immunoglobulin preparations containing capsule type-specific antibodies conferred protection to animals against group B streptococci of the corresponding capsule type Lancefield et al. 1975, supra, and Gotoff et al. supra. High antibody titers against the group B carbohydrate did not apparently correlate with reduced infection rate (Anthony et al., 1985, *J. Inf. Dis.* 151:221) nor were murine monoclonal antibodies to the group B carbohydrate antigen protective in vivo (Shigeoka et al., supra).

Murine monoclonal antibodies have also been made which bind to and opsonize several K1-positive *E. coli* strains regardless of their LPS serotypes (Cross et al., 1983, *J. Inf. Dis.* 147:68, Soderstrom, T. et al., 1983, *Prog. Allergy* 33:259, and Cross, A. S., et al., "The Importance of the K1 Capsule in Invasive Infections Cause by *Escherichia coli*," J. Inf. Dis., 149:184–193 (1984)). Moreover, these monoclonal antibodies have been found to be protective in mice against lethal challenges with *E. coli* K1 and Group B meningococcal organisms (Cross, supra and Soderstrom, supra). The antibodies, of the IgM isotype, were derived from mice immunized with polysaccharide obtained from *N. meningitidis* group B.

A mouse monoclonal antibody, while useful in treating mice, has major disadvantages for use in humans The human immune system is capable of recognizing any mouse monoclonal antibody as a foreign protein. This can result in accelerated clearance of the antibody and thus abrogation of its pharmacological effect (Levy, R. and Miller, R. A., "Tumor Therapy with Monoclonal Antibodies," *Fed. Proc.* 42:2650–2656 (1983)). More seriously, this could conceivably lead to shock and even death from allergic reactions analogous to "serum sickness." Clinical experience has shown that anti-mouse immunoglobulin responses have limited the utility of these antibodies in approximately one-half of the patients receiving mouse monoclonal antibodies for treatment of various tumors (Sears, H. F., et al., "Phase I Clinical Trial of Monoclonal Antibody in Treatment of Gastrointestinal Tumor," *Lancet* 1:762–764 (1982); and Miller, R. A., et al., "Monoclonal Antibody Therapeutic Trials in Seven Patients with T-Cell Lymphoma" Blood. 62:988–995 (1983)).

Accordingly, there remains a significant and urgent need for human monoclonal antibodies which are protective against infections due to gram-negative and gram-positive bacterial pathogens important in neonatal sepsis and meningitis The present invention overcomes prior difficulties and fulfills the need for such compositions and methods of treatment, prophylaxis, and diagnosis.

SUMMARY OF THE INVENTION

Novel methods and pharmaceutical compositions are provided for prophylactically treating a human patient susceptible to bacterial infection due to *E. coli* K1 or *N. meningitidis* group B or therapeutically treating a patient suffering from such infections The methods comprise administering an effective amount of a composition comprising a human monoclonal antibody, which antibody is capable of reacting with an accessible carbohydrate antigenic determinant of *E. coli* K1 or *N. meningitidis* group B. Novel methods are also provided for prophylactically or therapeutically treating a patient susceptible to or suffering from an infection caused by group B streptococci by administering an effective amount of a composition comprising a human monoclonal antibody or binding fragment thereof which is capable of binding specifically to the group B polysaccharide of group B streptococci. The pharmaceutical compositions for therapeutic or prophylactic use will preferably include a physiologically acceptable carrier, and may also contain any one or more of the following: additional human monoclonal antibodies capable of reacting with the same or other bacterial genera; a gamma globulin fraction from human blood plasma; a gamma globulin fraction from human blood plasma, where the plasma is obtained from a human exhibiting elevated levels of immunoglobulins reactive with one or more bacterial genera; and one or more antimicrobial agents.

Novel cell lines are provided which produce human monoclonal antibodies capable of binding the group B carbohydrate shared by different serotypes of group B streptococci. Novel cell lines are also provided which produce human monoclonal antibodies that bind to an accessible antigen comprising a carbohydrate moiety of *E. coli* K1. The monoclonal antibodies may also be capable of reacting with at least one other bacterial species. The bacterial species with which the human monoclonal antibodies cross-reacts may be gram-positive or gram-negative. In a particular embodiment the species with which the antibodies react are *E. coli* and *N. meningitidis* group B. In another embodiment the species are group B streptococcus and *E. coli*.

DESCRIPTION OF THE SPECIFIC EMBODIMENTS

In accordance with the present invention, novel cells capable of producing human monoclonal antibodies and compositions comprising such antibodies are provided, such compositions being nosocomial, neonatal or other infections, where individual antibodies typically react with carbohydrate epitopes present on said organisms. The subject cells have identifiable chromosomes in which the germ-line DNA from them or a precursor cell has rearranged to encode an antibody or receptor fragment thereof having a binding site for an antigenic determinant (epitope) on carbohydrate molecules found on a serotype or shared by one or more serotypes of the same bacterial species or two or more bacterial genera. In one embodiment, a monoclonal antibody binds to the group B carbohydrate shared by serotypes of group B streptococci, and may also be capable of binding to *E. coli*, for example. In another embodiment, a human monoclonal antibody binds to a capsular carbohydrate moiety on *E. coli* K1, and may also be capable cross-reacting with capsule of *N. meningitidis*, particularly *N. meningitidis* group B. These monoclonal antibodies can be used in a wide variety of ways, including for diagnosis, prophylaxis and therapy of bacterial disease.

Typically, the cells of the present invention will be cells capable of stable production of a human antibody in culture, particularly immortalized human lymphocytes that produce human monoclonal antibodies to carbohydrate determinants on accessible molecules of the bacterium. By "accessible" is meant that the carbohydrate determinants are physically available in the environment of use for direct interaction with the monoclonal antibodies. The monoclonal antibodies so provided are useful in the treatment or prophylaxis of serious disease caused by a wide range of bacterial infections Furthermore, those carbohydrate molecules that are released into the surrounding environment are also free to interact directly with the antibody molecules and be cleared via the reticuloendothelial system.

The compositions containing the monoclonal antibodies of the present invention will typically be useful in the therapeutic and prophylactic treatment of nosocomial, neonatal, and other infections. For neonatal use, such as for prophylaxis or therapy of neonatal sepsis and/or meningitis, the antibody compositions are desirably specific for two or more of the following bacterial organisms: *E. coli* K1, *N. meningitidis* group B, *S. agalactiae* group B, and *H. influenzae* type B. Desirably, the monoclonal antibodies will react with individual members or all of the members of a particular bacterial species, where the members may be distinguished by their surface epitopes, particularly LPS or capsule types, e.g. serotypes.

The unexpected discovery of human monoclonal antibody cross-reactivity across various bacterial species, including the clinically important species listed above, provides novel means for therapeutic and prophylactic treatments. By utilizing pre-selected cross-reactive antibodies in combination, a mixture of a few antibodies can be produced for treatment against a number of different species of infectious bacteria.

By way of example, and not of limitation, a mixture of two monoclonal antibodies, one cross-reactive with at least two bacterial species of clinical significance and the second cross-reactive with at least two or three different species, will be useful in treatment against four, five, six or more different species. Of course, it may be necessary to also add one or more monoclonal antibodies, each specific for just a single pre-selected bacterial species or particular serotype, for example, when monoclonal antibodies cross-reactive with that species are unavailable.

Preparation of monoclonal antibodies can be accomplished by immortalizing the expression of nucleic acid sequences that encode for antibodies or binding fragments thereof specific for a carbohydrate epitope present on the desired bacterial species. Typically, the monoclonal antibodies are produced by cell-driven Epstein-Barr Virus (EBV) transformation of lymphocytes obtained from human donors who are, or have been exposed to the respective gram-negative or gram-positive bacteria. The antibody-secreting cell lines so produced are characterized as continuously growing lymphoblastoid cells that possess a diploid karyotype, are Epstein-Barr nuclear antigen (EBNA) positive, and secrete monoclonal antibody of either IgG, IgM, IgA, or IgD isotype. The cell-driven transformation process itself is an invention assigned to Genetic Systems Corporation and is described in detail in U.S. Pat. No. 4,464,465 which is incorporated herein by reference. The monoclonal antibodies are preferably used intact, or may be used as receptor fragments, such as $F_v$, Fab, $F(ab')_2$, where such receptor fragment is part of an intact immunoglobulin molecule. Various methods are known for producing chimeric antibodies or entirely human antibodies where the receptor (binding) fragment of an antibody of the present invention may be joined to the constant regions ($F_c$) of antibodies of other species or of other human antibodies. See, for example, EP patent publication no. 173,494 and PCT publication WO86/01533 which are incorporated herein by reference.

Alternatively, cell lines producing the antibodies could be produced by cell fusion between suitably drug-marked human myeloma, mouse myeloma, or human lymphoblastoid cells with human B-lymphocytes to yield hybrid cell lines.

The cell lines of the present invention may find use other than for the direct production of the human monoclonal antibodies. The cell lines may be fused with other cells (such as suitably drug-marked human myeloma, mouse myeloma, or human lymphoblastoid cells) to produce hybridomas, and thus provide for the transfer of the genes encoding the human monoclonal antibodies. Alternatively, the cell lines may be used as a source of the DNA encoding the immunoglobulins, which may be isolated and transferred to cells by techniques other than fusion. In addition, the genes encoding the monoclonal antibodies may be isolated and used in accordance with recombinant DNA techniques for the production of the specific immunoglobulin in a variety of hosts. Particularly, by preparing cDNA libraries from messenger RNA, a single cDNA clone, coding for the immunoglobulin and free of introns, may be isolated and placed into suitable prokaryotic or eukaryotic expression vectors and subsequently transformed into a host for ultimate bulk production.

The lymphoblastoid or hybrid cell lines may be cloned and screened in accordance with conventional techniques, with the antibodies that are capable of binding to the epitopes of antigens from the desired bacterial serotypes, species or genera detected in the cell supernatants.

The monoclonal antibodies of this invention find particular utility as components of pharmaceutical compositions containing a therapeutic or prophylactic amount of at least one of the monoclonal antibodies of this invention in conjunction with a pharmaceutically effective carrier. A pharmaceutical carrier can be any compatible, non-toxic substance suitable for delivery of the monoclonal antibodies to the patient. Sterile water, alcohol, fats, waxes, and inert solids may be included in the carrier. Pharmaceutically accepted adjuvants (buffering agents, dispersing agents) may also be incorporated into the pharmaceutical composition. Such compositions can contain a single human monoclonal antibody reactive with carbohydrate epitopes of a bacterial species or shared by more than one species that cause, for example, nosocomial and neonatal infections (e.g., sepsis or meningitis). Alternatively, a pharmaceutical composition can contain two or more monoclonal antibodies to form a "cocktail." For example, a cocktail containing human monoclonal antibodies each protective against one or more gram-negative bacterial species responsible for human infections, could have activity against the great majority of the bacterial isolates commonly associated with particular clinical diseases. If desired, one or more of the monoclonal antibodies could be selected to be cross-reactive with gram-positive bacteria as well, making even broader product applications feasible.

Of particular interest are monoclonal antibody compositions for the treatment of neonatal and pediatric infections. Desirably, such compositions will react with at least two, usually at least three, and more usually at least four and usually including all of the following infection-causing bacterial species: *E. coli* K1, *N. meningitidis* group B, *S. agalactiae* group B, and *H. influenzae* type B.

Each of the compositions will include at least one, usually at least two, and more usually three to six human monoclonal antibodies, where at least one antibody reacts with carbohydrate epitopes (e.g., of the LPS molecules or group specific carbohydrates) of at least one species or shared by two or more bacterial genera and providing protection. The antibody may not bind to all serotypes of each bacterium, but may bind to one, two, three or more serotypes. Desirably, there will be at least one human monoclonal antibody which binds to an accessible carbohydrate moiety of a gram-negative bacterium, such as *E. coli* K1 or *N. meningitidis*, and at least one monoclonal antibody that binds to an accessible carbohydrate moiety of a gram-positive bacterium, such as the group B streptococcus.

The mole ratio of the various monoclonal antibody components will usually not differ one from the other by more than a factor of 100, more usually by not more than a factor of 25, often by not more than a factor of about 10 or 5, and will usually be in a mole ratio of about 1:1.2 to each of the other antibody components.

The human monoclonal antibodies may also find use individually, particularly where the pathogen has been identified or is limited to a narrow range of pathogens within the binding spectrum of the particular antibody.

The human monoclonal antibodies of the present invention may also be used in combination with other monoclonal antibodies (e.g., commonly assigned Great Britain patent application GB2,185,266A entitled "Monoclonal Antibodies Cross-Reactive and Protective Against *P. aeruginosa* Serotypes," published Jul. 15, 1987 and Great Britain patent publication GB2,192,185A entitled "Protective Anti-Flagellar Monoclonal Antibodies," published Jan. 6, 1988 which are incorporated herein by reference) as well as existing blood plasma products, such as commercially available gamma globulin and immune globulin products used in prophylactic or therapeutic treatment of bacterial disease in humans. Preferably, for immune globulins the plasma will be obtained from human donors exhibiting elevated levels of immunoglobulins reactive with various infectious bacterial genera. See generally, the compendium "Intravenous Immune Globulin and the Compromised Host," *Amer. J. Med.*, 76(3a), Mar. 30, 1984, pgs 1–231, which is incorporated herein by reference.

The monoclonal antibodies of the present invention can be used as separately administered compositions given in conjunction with antibiotics or antimicrobial agents. Typically, the antimicrobial agents may include a penicillin (e.g., carbenicillin, penicillin G, ampicillin, or the like) in conjunction with an aminoglycoside (e.g., gentamicin, tobramycin, amikacin or the like), but numerous additional agents (e.g., cephalosporins, such as cefepime or the like, sulfa drugs, etc.) well-known to those skilled in the art may also be utilized.

The human monoclonal antibodies and pharmaceutical compositions thereof of this invention are particularly useful for oral or parenteral administration. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, i.e., from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for intramuscular injection in adults could be made up to contain 1 ml sterile buffered water, and 50 mg of each of one or more monoclonal antibodies. A typical composition for intravenous infusion in adults could be made up to contain 250 ml of sterile Ringer's solution, and 150 mg of monoclonal antibody. Actual methods for preparing parenterally administrable compositions and adjustments necessary for administration to neonates will be known or apparent to those skilled in the art and are described in more detail in, for example, *Remington's Pharmaceutical Science*, 15th Ed., Mack Publishing Company, Easton, Pa (1980), which is incorporated herein by reference.

The monoclonal antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present human monoclonal antibodies or a cocktail thereof can be administered for the prophylactic and/or therapeutic treatment of bacterial infections. In therapeutic application, compositions are administered to a patient already infected, in an amount sufficient to cure or at least partially arrest the infection and its complications. An amount adequate to accomplish this is defined as a "therapeutically effective dose." Amounts effective for this use will depend upon the severity of the infection and the general state of the patient's own immune system, but generally range from about 0.1 to about 50 mg of antibody per kilogram of body weight with dosages of from 0.5 to 5 mg per kilogram being more commonly used. It must be kept in mind that the materials of this invention may generally be employed in serious disease states, that is life-threatening or potentially life-threatening situations, especially bacteremia and meningitis. In such cases, in view of the absence of extraneous substances and the absence of "foreign substance" rejections which are achieved by the present human monoclonal antibodies of this invention, it is possible and may be felt desirable by the treating physician to administer substantial excesses of these antibodies.

In prophylactic applications, compositions containing the present antibody or a cocktail thereof are administered to a patient not already infected by the corresponding bacteria to enhance the patient's resistance to such potential infection. Such an amount is defined to be a "prophylactically effective dose." In this use, the precise amounts again depend upon the patient's state of health and general level of immunity, but generally range from 0.1 to 25 mg per kilogram, especially 0.5 to 2.5 mg per kilogram.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Monoclonal antibodies of the present invention can further find a wide variety of utilities in vitro By way of example, the monoclonal antibodies can be utilized for bacterial typing, for isolating specific bacterial strains or fragments thereof, for vaccine preparation, or the like. For instance, human monoclonal antibodies of the present invention which bind to *E. coli* K1 and/or *N. meningitidis* group B may be useful alone or in combination with other antibodies in diagnosing cases of neonatal sepsis, meningitis, or other infections due to such organisms. Similarly, monoclonal antibodies which cross-react among the capsular serotypes of group B strepococci will be useful in diagnosing group B streptoccal disease. If the monoclonal antibodies also cross-react with other organisms additional tests may be necessary to identify or distinguish the particular organism detected in the sample.

For diagnostic purposes, the monoclonal antibodies may either be labeled or unlabeled. Typically, diagnostic assays of the invention entail detecting the formation of a complex through the binding of the monoclonal antibody to the carbohydrate of the organism. When unlabeled, the antibodies find use in agglutination assays. In addition, unlabeled antibodies can be used in combination with other labeled antibodies (second antibodies) that are reactive with the monoclonal antibody, such as antibodies specific for human immunoglobulin. Alternatively, the monoclonal antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available, and by way of example, some of the assays are described in U.S. Pat. Nos. 3,817,827; 3,850,752; 3,901,654; 3,935,074; 3,984,533; 3,996,345; 4,034,074; and 4,098,876, all of which are incorporated herein by reference.

Commonly, the monoclonal antibodies of the present invention are utilized in enzyme immunoassays, where the subject antibodies, or second antibodies from a different species, are conjugated to an enzyme. When a sample, such as human blood or lysate thereof, containing one or more bacteria of a certain genus or serotype, is combined with the subject antibodies, binding occurs between the antibodies and those molecules exhibiting the selected epitopes. Such cells may then be separated from the unbound reagents, and a second antibody (labeled with an enzyme) added. Thereafter, the presence of the antibody-enzyme conjugate specifically bound to the cells is determined. Other conventional techniques well known to those skilled in the art may also be utilized.

Kits can also be supplied for use with the subject antibodies in the detection of bacterial infection or for the presence of a selected antigen. Thus, the subject monoclonal antibody composition of the present invention may be provided, usually in a lyophilized form in a container, either alone or in conjunction with additional antibodies specific for other bacteria. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

The following experimental data and information are offered by way of example and not limitation.

EXAMPLE I

Example I demonstrates methods for the production of a human monoclonal antibody that is reactive with both the *E. coli* capsular type K1 and *N. meningitidis* group B polysaccharide and further demonstrates the protective activity of said antibody in vivo against a lethal challenge of homologous *E. coli* and *N. meningitidis* bacterial species.

A. Obtaining Suitable Human Cells

Suitable human B cells (lymphocytes) were obtained from the peripheral blood of an individual known to have harbored the disease cystic fibrosis Mononuclear cells were separated from the peripheral blood by standard centrifugation techniques on Ficoll-Paque (Boyum, A., "Isolation of Mononuclear Cells and Granulocytes From Human Blood," *Scand. J. Clin. Lab. Invest.* 21. Suppl. 97:77-89, (1968)) and washed twice in calcium-magnesium free phosphate buffered saline (PBS) prior to suspension in 1 ml of 90% fetal bovine serum (FBS) and 10% dimethyl sulfoxide and freezing at $-196°$ C. in liquid nitrogen.

When the mononuclear cells were to be transformed, an ampule containing $5 \times 10^7$ cells was rapidly thawed at 37° C. The cell suspension was added to 10 ml of Iscove's medium containing 15% FBS and centrifuged at room temperature for 10 min at $250 \times g$. The mononuclear cells were depleted of T cells (lymphocytes) using a modified E-rosetting procedure. Briefly, the cells were resuspended to a concentration of $1 \times 10^7$ cells/ml in PBS containing 20% FBS at 4° C. One ml of this suspension was placed in a $17 \times 100$ mm polystyrene round bottom tube to which was added $1 \times 10^9$ 2-aminoethyl-isothiouronium bromide (AET)-treated sheep red blood cells from a 10% (v/v) solution in Iscove's medium (Madsen, M. and Johnson, H. E., "A Methodological Study of E-rosette Formation Using AET Treated Sheep Red Blood Cells," *J. Immun. Methods* 27:61-74, (1979)). The suspension was vigorously mixed for 5-10 min at 4° C. and the E-rosetted cells were removed by centrifugation through Ficoll-Paque for 8 min at $2500 \times g$ at 4° C. E-rosette negative peripheral blood mononuclear cells (E$^-$PMBC) banding at the interface were washed once in Iscove's medium and resuspended in same containing 15% w/v FBS (g/ml), L-glutamine (2 mM/l), sodium pyruvate (1 mM/l), penicillin 100 IU/ml), streptomycin (100 $\mu$g/ml), hypoxanthine ($1 \times 10^{-4}$ M0, aminopterin ($4 \times 10^{-7}$ M), and thymidine ($1.6 \times 10^{-7}$ M). This medium is hereafter referred to as HAT medium.

B. Cell-Driven Transformation of Peripheral Blood Mononuclear Cells

Cell-driven transformation of the E$^-$PBMC was accomplished by cocultivating the E$^-$PBMC with a transforming cell line. The transforming cell line was an EBNA positive human lymphoblastoid cell line derived by ethylmethane sulphonate mutagenesis of the GM 1500 lymphoblastoid cell line. Selection in the presence of 30 $\mu$g/ml 6-thioguanine rendered the cells hypoxanthine-guanine phosphoribosyl transferase deficient and thus HAT sensitive. The cell line is denominated the 1A2 cell line and was deposited at the American Type Culture Collection (A.T.C.C.) on Mar. 29, 1982 under A.T.C.C. No. CRL 8119. 1A2 cells in logarithmic growth phase were suspended in HAT medium and combined with the E$^-$PBMC at a ratio of 30 1A2 cell per E$^-$PBMC. The cell mixture was plated into 10 round-bottom 96-well microtiter plates at a concentration of 62,000 cells/well in a volume of 200 $\mu$l/well, and the culture incubated at 37° C. in a humidified atmosphere containing 6% CO$_2$. Cultures were fed five days post transformation by replacement of half the supernatant with fresh HAT medium. The wells were observed every other day on an inverted microscope for signs of cell proliferation. Ten days after plating the cell mixture and after the 1A2 cells had died due to HAT selection, feeding of the the wells was accomplished with a new media formulation identical to HAT media except that it lacked the aminopterin component. Fifteen days post plating, it was observed that 100% of the wells contained proliferating cells and that in most of the wells, the cells were of sufficient density for removal and testing of supernatants for anti-*E. coli* or anti-*S. marcescens* antibody.

C. Detection of Specific Antibody Secreting Cells

Supernatants were screened for the presence of anti-*E. coli* or anti-*S. marcescens* antibodies using an enzyme-linked immunosorbent assay (ELISA) technique (Engvall, E., "Quantitative Enzyme Immunoassay (ELISA) in Microbiology," Med. Biol., 55:193-200, (1977)). The antigen plates consisted of a series of flat-bottom 96-well Immunlon 2 microtiter plates, the wells of which contained a mixture of either viable *E. coli* or *S. marcescens* serotypes affixed to the well surfaces with poly-L-lysine (PLL). Briefly, 50 $\mu$l of PLL (1 $\mu$g/ml) in PBS was added to each well for 30 min at room temperature (RT). The plates were washed three times with PBS and either PBS or 50 $\mu$l of a mixed bacteria suspension at O.D.$_{660}$-0.2 was added to each well. The plates were incubated at 37° C. for 60 min and washed 3 times with saline/0.02% Tween 20 (saline/T) to removed unattached bacteria. Various antigen plates used in the screen included: (1) a mixture of *E. coli* serotypes 01 (A.T.C.C. No. 23499) and 04 (A.T.C.C. No. 12791); (2) a mixture of *S. marcescens* serotypes 07, 015, 016 and 018 (all reference typing strains were obtained from the Communicable Disease Center (CDC) Atlanta, GA); and (3) a microtiter plate with no bacteria.

For the ELISA procedure, assay wells were first blocked with 200 $\mu$l of a mixture containing 5% w/v dry non-fat milk, 0.0001% Foam A, and 0.01% w/v Thimerosal in 500 ml PBS to prevent non-specific protein binding. After incubation for 1 hour at RT, the plates were washed three times with 200 $\mu$l/well/wash of saline/T. To each well was added 50 $\mu$l of a mixture containing 0.1% Tween 20 and 0.2% bovine serum albumin in PBS (PTB). Supernatants from wells of the culture plate were replica plated into corresponding wells of the antigen and control plates (50 $\mu$l/well) and the plates were incubated at RT for 30 min. The supernatants were then removed, plates were washed five times with saline/T, and 50 $\mu$l of biotinylated goat anti-human immunoglobulin (Ig)(TAGO #9303040 diluted 1:250 in PTB) was added to each well. After a 30 min incubation at RT the biotinylated reagent was removed, the wells washed five times with saline/T and 50 $\mu$l of a preformed avidin:biotinylated horseradish peroxidase complex (Vectastain ABC Kit, Vector Laboratories) was added to each well. After 30 min. at RT the Vectastain ABC reagent was removed, the wells were washed five times with saline/T, and 100 $\mu$l of substrate (0.8 mg/ml orthophenylenediamine dihydrochloride in 100 mM citrate buffer, pH 5.0 plus 0.03% H$_2$O$_2$ in deionized H$_2$O mixed in equal volumes just before plating) added to each well. After 30 min incubation in the dark, 50 $\mu$l of 3N H$_2$SO$_4$ was added to each well to terminate the reaction. Culture supernatants which contained antibody reactive with the bacteria coated plates were detected by measuring absorbance at 490 nm on a Dynatech MR 580 microELISA reader.

Culture supernatants from five transformations were analyzed by the above method resulting in the identification of four wells (5D4, 2C10, 9B10, and 8A8) which possessed activity on the *E. coli* serotype plate, but not on the *S. marcescens* or control plates. It was determined in subsequent ELISA's with individual *E. coli* serotypes, that these wells contained antibody reactive with, at least, the following coli serotypes: 01 (ATCC 23499), 07:K1 (ATCC 12792), 016:K1 (ATCC 23511) and 050 (CDC 1113-83), but not 04, 06:K2, 08:K8, 09:K9 or 022:K13 (A.T.G.C. Nos. 12792, 19138, 23501, 23505 and 23517, respectively). Due to its better performance during the cloning procedure and increased antibody production, the 9B10 monoclonal antibody was selected for further analysis.

D. Cloning of Specific Antibody Producing Cells

The cells in well 9B10 were subjected to several rounds of cloning until all clonal supernatants assayed by the above ELISA procedure gave a positive reaction on selected *E. coli* serotypes. Cells were cloned by limiting dilution in round-bottom 96-well plates in the absence of feeder cells. Media consisted of Iscove's medium containing 15% v/v FBS, L-glutamine (2 mM/1), sodium pyruvate (1 mM/1), penicillin (100 IU/ml), and streptomycin (100 µg/ml). Cultures were fed every three days by replacement of half the supernatant with fresh media. In general, wells were of sufficient lymphoblastoid cell density between 2 and 3 weeks post-plating for analysis of anti-*E. coli* serotype specificity.

Prior to filing of this patent application, the continuous transformed human cell line identified as 9B10 was deposited with the American Type Culture Collection, Rockville, MD as A.T.C.C. No. CRL 9006.

E. Characterization of Monoclonal Antibody 9B10

The finding that the monoclonal antibodies from each of the clones (5D4, 2C10, 9B10 and 8A8) reacted with the identical group of *E. coli* O-antigen serotypes, indicated that these antibodies were directed against a bacterial surface structure common to these serotypes. Several approaches were used to define the surface structure common to these *E. coli* serotypes. As set forth, two (07:K1 and 016:K1) of the four *E. coli* serotypes identified by the 9B10 antibody possessed the K1 capsular serotype, while the other two (01 and 050) had not been typed for their K-antigen serotype. Thus, the possibility was pursued that the 9B10 antibody contained reactivity to the K1 antigen and that the *E. coli* strains possessing the O-antigen serotypes 01 and 050 also possessed the K1 capsular serotype.

Others have taken advantage of the thermolability of the K1 capsule to establish its presence. Heating of K1 positive *E. coli* serotypes in a boiling water bath at 100° C. for 60 minutes removes the subsequent ability of these strains to react with anti-K1 sera and enhances their ability to react with anti-O antigen sera (Orskov, F. and Orskov, I., "Serotyping of *Escherichia coli*." in *Methods in Microbiology*, Vol. 14, T. Bergan, ed., Academic Press, London (1984) pp. 44–105). The reciprocal effects of boiling are most likely due to the removal of the capsule and the increased accessibility of antibody for lipopolysaccharide (LPS) molecules. The *E. coli* K1 positive serotypes (07 and 016) and the non-K1 typed serotypes (01 and 050) were heated as set forth and reacted with the 9B10 antibody and LPS serotype specific heterologous sera (Difco Bacto-*E. coli* Typing Reagents) in the ELISA procedure. Heat treated organisms lost all reactivity to the 9B10 antibody and had increased their reactivity with their homologous LPS serotype specific sera, while non-treated (control) organisms remained strongly reactive with 9B10 culture supernatants and poorly reactive with their respective LPS serotype specific antisera.

The polysaccharide (carbohydrate) from *N. meningitidis* group B bacteria (a homopolymer of sialic acid, alpha 2, 8-linked poly-N-acetyl neuraminic acid) has been proven to be chemically and antigenically homogeneous with the *E. coli* K1 polysaccharide (Grados, O. and Ewing, W. H., "Antigenic Relationship between *Escherichia coli* and *Neisseria meningitidis*." 1973, *J. Immunol.* 110:262–268). These data suggest that if the 9B10 monoclonal antibody contains specificity to *E. coli* K1 capsule then the antibody should also contain specificity to meningitidis group B polysaccharide and further, that monoclonal antibodies containing specificity to the Group B polysaccharide of *N. meningitidis* should also demonstrate reactivity to strains possessing the K1 capsule. Two experimental protocols were used that tested for (1) the ability of the 9B10 antibody to react with *N. meningitidis* and (2) the ability of an antibody against *N. meningitidis* group B polysaccharide to react with the four *E. coli* 9B10 reactive serotypes.

Highly purified Group B polysaccharide (Connaught Laboratories, Toronto, Canada) and viable *N. meningitidis* group B bacteria were reacted with the 9B10 antibody in an ELISA as set forth. The 9B10 monoclonal antibody strongly reacted against both antigen preparations. To prove the converse specificity, a commercially available meningitidis group B test kit (Direct Antigen Detection System, Hynson, Westcott, and Dunning, Baltimore, MD), that utilizes latex spheres coated with an antibody to the Group B polysaccharide, was used. In agglutination assays using the 9B10 positive *E. coli* serotypes, all four serotypes demonstrated strong reactivity with the antibody coated spheres. *E. coli* serotypes known to be K1-antigen negative were also negative in this test system. Collectively, these data indicate that the 9B10 monoclonal antibody is reactive with the *E. coli* K1capsule and the type-specific carbohydrate on meningitidis group B. Further, since many of these assays were performed with intact, viable bacteria, it can be inferred that monoclonal antibody 9B10 is specific for some portion of an externally exposed region of the poly-sialic acid molecule.

The isotype of the 9B10 monoclonal antibody was determined in an ELISA procedure similar to the specificity tests described above except that the antigen plate contained a pool of PLL immobilized *E. coli* K1 positive serotypes. Positive reaction of the 9B10 monoclonal antibody with the K1 positive *E. coli* serotypes was observed only with the anti-IgM reagent, demonstrating an IgM isotype for the monoclonal antibody. It will be appreciated by those skilled in the art that if the process of this Example were repeated several times and the isotypes of K1-specific monoclonal antibodies so obtained were determined, one would find additional isotypes, e.g., IgM and IgG isotypes (see. e.g., Frosch et al., 1985, Proc. Natl. Acad. Sci. USA 82:1194).

F. In Vitro Activity

In vitro functional activity of the 9B10 monoclonal antibody was examined in an opsonophagocytic assay which compared the bacteriocidal activity of the antibody in the presence and absence of both human neutrophils and human complement.

Bacteria were prepared by either inoculating 10 ml of tryptic soy broth (TSB) with 50 µl of an overnight broth culture. For broth cultures, the tubes were incubated at 37° C. on a shaker for 3 hours at which time 1.5 ml of the culture was centrifuged for 1 min at 10,000×g, the spent culture media discarded, and the pellet was suspended in 3.5 ml of Hank's balanced salt solution containing 0.1% gelatin and 5 mM HEPES (HBSS/Gel). The bacterial concentrations were adjusted to $3 \times 10^3$ bacteria/ml by measuring the $O.D._{660}$ and making the appropriate dilutions (approximately 1:50,000). Human neutrophils were isolated according to van Furth and Van Zwet ("In Vitro Determination of Phagocytosis and Intracellular Killing by Polymorphonuclear and Mononuclear Phagocytes," in *Handbook of Experimental Immunology*, Vol. 2, D. M. Weir, ed., 2nd edition, Blackwell Scientific Publications, Oxford, 36.1–36.24(1973)) with several modifications. Buffy coat from 10 ml of heparinized blood was underlayed with Ficoll-Pacque and centrifuged. The red blood cell (RBC) pellet was washed once with RPMI 1640 medium and resuspended in an equal volume of 37° C. PBS. Three ml of this suspension was added to 6 ml of 2% dextran (in 37° C. PBS) and the contents gently but thoroughly mixed end over end. After a 20 min incubation at 37° C. to allow the RBC's to sediment, the supernatant (containing neutrophils) was removed, washed twice in 4° C. PBS, once in HBSS/Gel, and suspended in same to $5 \times 10^7$ neutrophils/ml. For the complement source used with *E. coli*, human serum was twice adsorbed with live bacteria pools (Bjornson, A. B. and Michael, J. G., *J. Inf. Dis.*, 130Suppl:S119–S126 (1974)) corresponding to the organisms used in the assay. This serum was further adsorbed with boiled Zymosan (Bjornson, ibid) to remove the serum component properdin, a molecule necessary for the activation of the alternate complement pathway.

Plates used to quantify the number of surviving/destroyed bacteria were prepared beginning with warming of 24 well plates at 37° C. for 3.5 hours. A 0.4% solution of agarose in TSB was prepared by autoclaving the mixture for 5 min and allowing it to cool to 50° C. in a water bath. Approximately 15 min before the end of the final incubation period in the opsonophagocytosis assay, a 24 well plate was removed from the 37° C. incubator, placed on a 42° C. hot plate and 0.4 ml of TSB/agarose was added to each well. The plate was immediately returned to the 37° C. incubator such that the agarose never cooled below 37° C.

For the assay, 25 μl of 9B10 culture supernatant and 25 μl of an appropriate bacterial strain were added in duplicate to 96 well round bottom microtiter plates and incubated at RT for 30 min. This was followed by the addition of 15 μl of human complement, 15 μl of human neutrophils ($5 \times 10^6$/ml), and 70 μl HBSS/Gel. The entire surface of the plate was wiped with a sterile cotton swab, an adhesive plastic plate sealer was applied to securely cover the entire plate and interwell areas, and the plate was rotated at 37° C. for 1 hour. After incubation, the plate was centrifuged for 5 min at 100×g, the plate sealer was gently removed, and the plate surface was dried with a sterile cotton swab dipped in 70% ethanol. Fifty microliters was removed from each microtiter well and was added to individual wells of the 24 well quantitation plates which already contained the 0.4 ml/well of melted (38°–40° C.) 0.4% TSB/agarose. These plates were placed on a flatbed shaker for 1 min at 150 RPM and the agarose was allowed to harden for 15 min at RT. Finally, a 0.4 ml TSB/agarose overlay was added to each well, followed by a hardening period of 15 min at 4° C. before the plates were incubated overnight at 37° C. After 18 hours the colonies were enumerated and the data was reported as colony forming units (CFU) for each condition.

K1 positive *E. coli* serotypes were only inactivated in the presence of monoclonal antibody 9B10, an active complement source, and human neutrophils (Table 4). When this experiment was repeated with several K1 negative *E. coli* serotypes, no bacterial destruction assay was observed (data not shown) thus demonstrating the K1 specificity of monoclonal antibody 9B10 and its capacity to opsonize bacteria and promote their phagocytosis. Since the combined action of opsonins (specific antibodies) and polymorphonuclear leukocytes (neutrophils) appeared to be the primary mechanism for immunity to K1 positive *E. coli* serotypes, these data suggested that antibody 9B10 would, after appropriate administration, provide protection against a lethal challenge with any *E. coli* K1 encapsulated serotypes, regardless of its O-antigen serotype.

TABLE 4

| Bacteria | Neutrophils | Antibody | Complement | Destruction of Input Bacteria % |
|---|---|---|---|---|
| *E. coli* 01:K1[a] and 018:K1 | + | 9B10 | −[b] | 0 |
| *E. coli* 01:K1 and 018:K1 | + | 6F11[c] | + | 0 |
| *E. coli* 01:K1 and 018:K1 | − | 9B10 | + | 0 |
| *E. coli* 01:K1 and 018:K1 | + | 9B10 | + | 99% |
| *N. meningitidis* Group B | + | 9B10 | − | 0 |
| *N. meningitidis* Group B | + | 6F11 | + | 0 |
| *N. meningitidis* Group B | − | 9B10 | + | 0 |
| *N. meningitidis* Group B | + | 9B10 | + | 99% |

[a]Results presented are derived from individual experiments with each strain of *E. coli*.
[b](−) = heat-inactivated (56° C. for 30 min) human complement.
[c](6F11) = culture supernatant containing an IgM human monoclonal antibody to *Pseudomonas aeruginosa* Fisher type 2.

G. Antibody Purification

9B10 and negative control (6F11, human IgM monoclonal antibody specific *Pseudomonas aeruginosa* Fisher immunotype 2) antibodies were first concentrated from spent culture supernatants by precipitation with solid ammonium sulphate (50% final concentration) (Good, A. J. et al., "Purification of Immunoglobulins and Their Fragments," in *Selected Methods in Cellular Immunology*, Mishell, B. B. and Shiigri, S. M., eds., W. H. Freeman and Company, San Francisco, CA (1980) 279–286). Precipitated material was reconstituted in sterile water and extensively dialyzed against PBS.

The IgM antibody in the ammonium sulphate salt precipitate was purified by affinity chromatography on a murine monoclonal anti-human IgM antibody affinity column. To prepare the column, one gram of dehydrated cyanogen bromide activated Sepharose 4B (Pharmacia) was mixed with 15 ml ice cold 1 mM HCl in distilled water. The hydrated gel was washed in 30 ml coupling buffer (0.1 M carbonate ($NaHCO_3$) in 0.5 M NaCl, pH 8.2), drained to form a moist cake and was combined with the ammonium salt precipitate dissolved in 1–3 ml of coupling buffer. The gel suspension was mixed end-over-end for 2 hr at RT and subsequently centrifuged at 200×g for 5 min. To block still available reactive sites, the supernatant was removed, 10 ml of 1 M ethanolamine was added to the gel, and mixing was continued as above. The suspension was centrifuged at 200×g for 5 min and the supernatant was discarded. The gel was prepared for use with 1 wash in 0.1 M acetate/saline buffer (6.8 g sodium acetate trihydrate and 14.6 g NaCl were dissolved in 500 ml distilled water containing 2.9 ml glacial acetic acid, pH 4.0), two washes in coupling buffer, and two washes in PBS. The gel was poured into a Pharmacia C10/10 column and stored at 4° C. until use.

To purify the immunoglobulin, 0.5 ml of salt fractionated material was diluted to 2.0 ml in PBS and was added to the affinity column. Following sample loading, the column was washed with PBS, pH 8.0 until the absorbancy monitor indicated no further protein in the flow-through. The bound antibody was eluted with 2 M $MgCl_2$ in PBS, the protein concentration was determined for each fraction at $O.D._{280}$, and the peak fractions pooled. The antibody containing fraction was desalted on a G-25 Sephadex column and, if necessary, was concentrated by microconcentration centrifugation (Centricon 30, Amicon Corp., Danver, MA) to 1–2 mg/ml. The final preparation was tested for purity by SDS-polyacrylamide gel electrophoresis followed by silver nitrate staining of proteins (Morrissey, J. H., "Silver Stain for Proteins in Polyacrylamide Gels: A Modified Procedure with Enhanced Uniform Sensitivity," Anal. Biochem., (1981) 117:307–310), and for antibody activity by Elisa as stated herein.

H. In Vivo Activity

To test the above hypothesis, animal protection studies were performed with the 9B10 antibody and several K1 positive and K1 negative E. coli serotypes, as well as a N. meningitidis group B serotype (strain H313, obtained from Dr. Carl Frasch, Laboratory of Bacterial Polysaccharides, Office of Biologics, Food and Drug Administration, Bethesda, MD).

For each bacteria challenge, female, outbred Swiss-Webster mice weighing between 20 and 22 gm were divided into three groups of ten mice each. A representative experiment was performed as follows:

| Group | Bacteria | Antibody |
|-------|----------|----------|
| A | E. coli K1 | 9B10 |
| B | E. coli K1 | 6F11 |
| C | E. coli K2 | 9B10 |
| E | N. meningitidis group B | 6F11 |
| F | N. meningitidis group B | 9B10 |

Each group receiving antibody was injected intravenously with 200 μl of sterile PBS containing 25 μg of purified antibody. Two hours later, all animals were challenged intraperitoneally with 300 μl of live bacteria containing 3 LD50 of their respective bacterial strain. The bacterial suspension had been prepared from a broth culture in logarithmic phase growth, from which the bacteria was centrifuged, washed twice in PBS, and resuspended to the appropriate concentration in PBS. Animals were observed for a period of five days. Twenty-four to forty-eight hours post-challenge all animals in Group (irrelevant antibody) and Group C (irrelevant organism) were dead. In contrast, those animals that had received the 9B10 (Group A) antibody were all alive and symptom free (Table 5).

TABLE 5

| Challenge Bacteria | Antibody | Survival/ Challenge | % Survival |
|---|---|---|---|
| E. coli K1 | 9B10 | 10/10 | 100% |
| E. coli K1 | 6F11[a] | 0/10 | 0% |
| E. coli K2[b] | 9B10 | 0/10 | 0% |
| N. meningitidis group B | 9B10 | 5/5 | 100% |
| N. meningitidis group B | 6F11 | 0/5 | 0% |

[a] 6F11 antibody is specific to Pseudomonas aeruginosa Fisher immunotype 2 and serves as negative control antibody.
[b] E. coli K2 is not reactive with the 9B10 antibody and serves as nonspecific control organisms.

These data demonstrate that the human monoclonal antibody 9B10 is able to protect mice from lethal challenges with bacteria belonging to two different gram-negative bacterial species. The intergenus cross-protective antibody was able to passively protect against infection by organisms belonging to the gram-negative bacterial species E. coli and N. meningitidis group B.

Using the procedures set forth in this Example, a second transformed cell line was produced which also secreted a human monoclonal antibody reactive with capsular antigens of both E. coli K1 and N. meningitidis group B. This monoclonal antibody, designated 5E1, was of the same isotype as antibody 9B10, exhibited similar in vitro characteristics, and protected animals prophylactically and therapeutically against challenge by homologous E. coli K1 strains. Using the methods and compositions of the present invention it would be within the ability of one skilled in the art to isolate additional cell lines which secret monoclonal antibodies possessing characteristics similar to those described herein.

EXAMPLE II

Example II demonstrates methods for the production of a human monoclonal antibody that possesses intergenus cross-reactivity against members of the species E. coli, Enterobacter cloacae (E. cloacae) and group B streptococcus. Further, this Example demonstrates an antibody cross-reactive with species belonging to the two main bacteria divisions; gram-negative (E. coli and E. cloacae) and gram-positive (group B streptococcus). Even further, this Example demonstrates the in vivo protective activity of said antibody against a lethal challenge of homologous E. coli, and group B streptococcus serotypes. The process of Example I (essentially described in parts A through F) was repeated to produce a human monoclonal antibody that was cross-protective against infections caused by the bacteria described herein, except that it was necessary to make specific modifications to characterize and assay the antibody described in this Example. The following are changes in assay procedures and the results obtained with the monoclonal antibody described herein.

Supernatants were screened for the presence of anti-group B streptococcus antibodies using an enzyme-linked immunosorbent assay (ELISA) technique as described in Example I. The antigen plates consisted of a series of flat-bottom 96-well Immunolon 2 microtiter plates, the wells of which contained mixtures of group B streptococci capsule types affixed to the well surfaces with poly-L-lysine (PLL). Various antigen plates used in the screen included: (1) a mixture of group B streptococcus types Ia (A.T.C.C. No. 12400), Ib (A.T.C.C. No. 12401), Ic (A.T.C.C. No. 27591); (2) a mixture of types II (A.T.C.C. No. 12973) and III (clinical isolate obtained from Dr. C. Wilson, Children's Orthopedic Hospital, Dept. Infectious Disease, Seattle, WA); and (3) a microtiter plate with no bacteria.

Culture supernatants from two transformations were analyzed by the above method resulting in the identification of one well (4B9) which possessed activity on both group B streptococcus typing plates, but not the control plates It was determined in subsequent ELISA's with individual group B streptococcus types, that this well contained antibody reactive with all five reference typing strains.

Thus, in this experiment one cloned transformed human cell line was achieved which is continuous (immortal) and secretes a human monoclonal antibody to a determinant on the surface of the group B streptococcus types set forth.

Prior to filing of this patent application, the continuous transformed human cell line identified as 4B9 was deposited with the American Type Culture Collection, Rockville, MD as A.T.C.C. No. CRL 9008.

Antibody from the cloned 4B9 cell line was assayed for cross-reactivity to gram.negative and gram-positive bacteria by a modification of the standard immunoblotting technique. Specifically, cross-reactivity to the bacteria *E. coli, K. pneumoniae, S. marcescens, E. aerogenes, E. cloacae, H. influenzae,* and *S. aureus* was investigated by spotting bacteria onto a gridded nitrocellulose paper disc, reacting the disc containing the bacteria with said antibody, and developing the antibody reactions with an alkaline phosphatase/nitroblue tetrazolium enzyme system (as described in Example I).

From these experiments, the 4B9 antibody was observed to possess cross-reactivity with particular gram-negative bacterial species. This antibody reacted with the *E. coli* LPS serotypes 04, 07, 018, and 025, and the *E. cloacae* clinical isolates Thus the human monoclonal antibody 4B9 possesses intergenus cross-reactivity between the gram.negative and gram-positive bacteria belonging to the species *E. coli, E. cloacae,* and group B streptococcus.

The finding that the monoclonal antibody cross-reacted with several different bacterial genera belonging to both gram-positive and gram-negative bacterial divisions, suggested the antibody was directed against a shared protein or carbohydrate. The biochemical characterization of the molecular species recognized by the 4B9 antibody was accomplished by immunoblot analysis. For analysis of the gram-negative genera, washed bacteria were extracted in deoxycholate as described in Example I. For the gram-positive bacteria, 1.0 L of bacteria cultured for 6 hours in modified Todd-Hewitt Broth (Difco, Todd-Hewitt Broth containing 2.8 gm/L anhydrous sodium phosphate, pH 7.8) at 37° C. were harvested by centrifugation and washed three times in PBS. The bacteria were resuspended in 85 ml of protoplast medium (40% sucrose w/v in 0.03 M potassium phosphate buffer, pH 6.8 containing 10 mM $MgCl_2$) and the suspension was warmed to 37° C. for 10 min. Approximately 3000 units of the mutanolysin (SIGMA) were added and the mixture was shaken at 37° C. for 90 min or until the $OD_{660}$ of the suspension had been reduced by >90%. The digested material was centrifuged at 2000×g for 15 min for RT and the supernatant was dialyzed against PBS for 48 hr (Young, M. K. and Mattingly, S. J., "Biosynthesis of Cell Wall Peptidoglycan and Polysaccharide Antigens by Protoplasts of Type III group B streptococcus, "*J. Bact.* (1983) 154:211-220). The dialysate was concentrated ten-fold by positive pressure dialysis through a PM-10 filter (Amicon Corp., Danvers, MA).

Carbohydrates binding to wheat germ agglutinin were purified by affinity chromatography on a wheat germ lectin Sepharose 6MB column (SIGMA). The bound digest, described herein, was eluted from the column with 10 ml of 0.1 M N-acetylglucosamine and the eluate was dialyzed against distilled water at 4° C. The affinity purified eluate was dried by lyophilization and the dry weight of the resulting material was obtained (Gray, B. M., et al., "Interaction of Group B Streptococcal Type-Specific Polysaccharides with Wheat Germ Agglutinin and Other Lectins," *J. Immunol. Meth.* (1984) 72:269-277). Positive reactions were noted in all tracks that contained deoxycholate extracts of the bacteria described herein. In those tracks containing extracts from gram-negative bacteria, the 4B9 antibody appeared to recognize a series of regularly spaced molecular entities giving rise to a ladder-like pattern on the immunoblot. The profile from the tracks containing extracts of the gram-negative bacteria was entirely consistent with that seen in polyacrylamide gel electrophoretic analysis of LPS in the presence of SDS, where it has been demonstrated that the heterogenous size profile exhibited by the bands is due to a population of LPS molecules differing by weight increments equivalent to the number of O-antigenic oligosaccharide side chain units present per molecule (Pavla, E. T. and Makela, P. H., supra and Goldman, R. D. and Leive, L., supra). In those tracks containing extracts from the group B streptococcus types, the 4B9 antibody appeared to recognize components present on a broad band. The profile from the tracks containing extracts of the gram-negative bacteria was consistent with that seen in polyacrylamide gel electrophoresis analyses of carbohydrate moieties that demonstrate extensive molecular weight heterogeneity with a frequently repeating specific sugar sequence (Vmir, E. R. et al., supra and Holden, K. G., supra). These data indicate that the monoclonal antibody 4B9 is directed against an antigenic determinant shared by molecules found on some serotypes of *E. coli, E. cloacae,* and group B streptococci.

To further define the molecular nature of the antigen, the deoxycholate extracts were treated with proteolytic enzyme Proteinase K prior to their electrophoresis (Eberling, W., supra). The immunoblot patterns observed after Proteinase K treatment were identical to those patterns observed without treatment and thus suggest that the antigen reactive with the 4B9 antibody is not protein in nature.

To specifically address whether 4B9 reacted with a carbohydrate epitope, the electrotransferred deoxycholate and wheat germ agglutination affinity purified samples were subjected to mild periodate oxidation prior to reacting the nitrocellulose paper with antibody (see EXAMPLE I). Electro-blotted deoxycholate extracts treated in this manner were no longer reactive with the 4B9 monoclonal antibody. These data strongly indicate that the epitope recognized by this antibody is a carbohydrate moiety present in molecules possessed by both the gram-negative and gram-positive bacteria described herein.

Two procedures were used to further characterize the antigen target for antibody 4B9 on group B streptococcus. Cross-immunoelectrophoresis (XIEP) with immunoblotting was used to identify the specific carbohydrate extracted from whole bacteria. Sugar competition binding studies identify sugars that characteristically block antibody reactivity with known group B streptococcal antigens (Anthony, B. F., et al., 1985, *J. Inf. Dis.* 151:221).

For crossed immunoelectrophoresis, 12 ml of 1% agarose (SeaKem HGT; GMC Corp., Rockland, ME) in Monthony buffer (Monthony, J. F., et al., 1978, Clin. Chem., 24:1825) was poured onto an 84×94 mm glass plate. Wells punched in the solidified gel were flush with soluble antigen, and the first XIEP dimension was run on an LKB Multiphore electrophoreis unit at 200 V, 10° C., 2 V/cm for 18 h. After repeated washing in saline and press/blotting, gels were either dried onto Gelbond (GMC Corp.) and stained with Crowle's Double Stain (Crowle, A. J., et al., 1977, *J. Immunol. Meth.* 17:379) or used to prepare blots. XIEP gel protein precipitates were passively transferred to nitrocellulose. The pressed gels were reswelled in 0.1 M glycine-HCl, pH 2.5 for 15 min., removed from the glass plates, and sandwiched between nitrocellulose and blot paper. Sandwiches are prepared as follows: two sheets of Whatman 3MM blotting paper soaked in glycine-HCl were layered onto a glass plate, the reswollen XIEP gel was laid on top and was carefully overlaid with nitrocellulose sheets soaked in electrophoretic transfer buffer (25 mM Tris, 192 mM glycine., pH 8.3 with 20% methanol), and the nitrocellulose sheets were covered with four sheets of dry blotting paper and a glass plate. After 15 min., the nitrocellulose was blocked with phosphate buffered saline containing 0.02% Tween-20 for at least 1 h. Gels blotted onto nitrocellulose paper were immersed for 1 h at room temperature in culture supernatants containing monoclonal antibodies. After washing, antibody binding was detected using an ELISA based substrate system as previously described.

Cross-immunoelectrophoresed group B streptococcal wall digests resolved into predominantly two peaks. The more anodal peak reacted predominantly with type-specific capsule antibodies, and the more slowly migrating antigens reacted with group B carbohydrate anti-bodies. Digests of a group B streptococcus type III encapsulated strain (COH 31r/s) were precipitated by monospecific capsule or group carbohydrate antisera, whereas a capsule deficient mutant (COH 31-15) reacted with only the group B antisera.

The precipitated complexes were passively transferred to nitrocellulose paper and antibody 4B9 was immunoblotted by routine immunoblot techniques. Using digests from several encapsulated clinical isolates with different capsule types, antibody 4B9 reacted with antigen that migrated to the same locations as the group B carbohydrate peak from strain COH 31-15 wall digest, as well as a commercially available, purified group B carbohydrate preparation (Difco) A negative control monoclonal antibody specific for LPS of *P. aeruginosa* did not react with any antigen preparation.

Sugar competition assays also identified the group B carbohydrate as the ligand for antibody 4B9. Purified antibody 4B9 or the *P. aeruginosa* control antibody were mixed with individual sugars (α-L-rhasmnose, D-glucitol, D-galactose, N-acetylglucosamine, and methyl-α-D-mannopyranoside) at final concentrations of 0.1 μg/ml antibody and 20 mg/ml sugar. Antibody and sugar mixtures were assayed in the standard ELISA (described above). The specificity of the blocking reactions was demonstrated by adsorbing identical antibody dilutions with an equal volume of packed, viable non-typable group B streptococci or control (*P. aeruginosa*) bacteria for 1 h at 4° C. The supernatants recovered after centrifugation were sterilized using Centrex centrifugal filters (Schliecher and Schuell), and were assayed by ELISA.

The group B, but not the type-specific antigens, contain α-L-rhamnose. Competition by this sugar only blocks antigen binding by group B carbohydrate antibodies (Anthony, B. F., supra). Aliquots of antibody 4B9 was incubated with high concentrations of rhamnose, glucitol, galactose, or N-acetylglucosamine. ELISA binding assays demonstrated that only rhamnose interfered with antibody 4B9 reactivity against a type Ia or type III isolate (Table 6). Only the group B streptococcal strains adsorbed the same antibody activity blocked by rhamnose As the antibody 4B9 cross reacts with serotypes of *E. coli*. it should be noted that *E. coli* O-serotypes 4, 7, 18, and 25 are known to contain rhamnose in their O-side chains (Vjacheslav, L., et al., 1984, *Carboh. Res.* 126:249-259; Gupta, D. S. et al., 1984, *Inf. Immun.* 45:203-209; Kenne, L , et al., 1983, *Carboh. Res.* 122:249-256; and Schmidt, M. A. et al., 1983, *Eur. J. Biochem.* 137:163-171), suggesting that rhamnose comprises at least a portion of the epitope recognized by antibody 4B9.

TABLE 6

| Capsule Type | COMPETING SUGAR | | | | |
|---|---|---|---|---|---|
| | None | Rhamnose | Glucitol | Galactose | N-acetyl-glucosamine |
| Ia | 0%[a] | 95% | 14% | 3% | 5% |
| III | 0% | 93% | 18% | 10% | 10% |

[a]Values are percentage decrease from maximal binding (100%), and are obtained using the formula:

$$\left(1 - \frac{\text{(ELISA value in presence of test competing sugar)}}{\text{(ELISA value in absence of test competing sugar)}}\right) \times 100$$

The isotype of the 4B9 monoclonal antibody was determined in an ELISA procedure similar to the specificity tests described above except that the antigen plate contained a pool of PLL immobilized group B streptococcus types II and III. Positive reaction of the 4B9 monoclonal antibody with the group B streptococcus strains was observed only with the anti-IgM reagent, demonstrating an IgM isotype for the monoclonal antibody.

In vitro functional activity of the 4B9 monoclonal antibody was examined in an opsonophagocytic assay which compared the bacteriocidal activity of the antibody in the presence and absence of both human neutrophils and human complement.

The bacterial strains used herein were only inactivated in the presence of monoclonal antibody 4B9, an active complement source, and human neutrophils (Table 7). When this experiment was repeated with several non-4B9 reactive bacterial serotypes, no bacteria destruction was observed, thus demonstrating the functional specificity of monoclonal antibody 4B9 and its capacity to opsonize bacteria and promote their phagocytosis. Since the combined actions of opsonins (specific antibodies) and polymorphonuclear leukocytes (neutrophils) appeared to be the primary mechanism for immunity to these bacterial strains, these data suggest that antibody 4B9, would, after appropriate administration, provide protection against lethal challenges with the bacteria strains described herein.

TABLE 7

| Bacteria | Neutrophils | Antibody | Complement | % Destruction of Input Bacteria |
|---|---|---|---|---|
| E. coli 018 and 025[a] | + | 4B9 | −[b] | 0 |
| E. coli 018 and 025 | + | 6F11[c] | + | 0 |
| E. coli 018 and 025 | − | 4B9 | + | 0 |
| E. coli 018 and 025 | + | 4B9 | + | 85% |
| E. cloacae Isolates | + | 4B9 | − | 0 |
| E. cloacae Isolates | + | 6F11 | + | 0 |
| E. cloacae Isolates | − | 4B9 | + | 0 |
| E. cloacae Isolates | + | 4B9 | + | 85% |
| Group B Strep.[a] Types Ia and III | + | 4B9 | − | 0 |
| Group B Strep. Types Ia and III | + | 6F11 | + | 0 |
| Group B Strep. Types Ia and III | − | 4B9 | + | 0 |
| Group B Strep. Types Ia and III | + | 4B9 | + | 85% |

[a] Results are derived from individual experiments with each strain.
[b] (−) = heat-inactivated (56° C. for 30 min) human complement.
[c] (6F11) = culture supernatant containing an IgM human monoclonal antibody to P. aeruginosa Fisher type 2.

To test the above hypothesis, animal protection studies were performed with the 4B9 antibody and at least one organism from each genus described herein.

From each gram-negative bacteria challenge, female, outbred Swiss-Webster mice weighing between 20 and 22 gm were divided into three groups of ten mice each. A representative experiment was performed as follows:

| Group | Bacteria | Antibody |
|---|---|---|
| A | E. coli 018 | 4B9 |
| B | E. coli 018 | 6F11 |
| C | S. marcescens 014 | 4B9 |

Each group receiving antibody was injected intravenously with 200 µl of sterile PBS containing 25 µg of purified antibody. Two hours later, all animals were challenged intraperitoneally with 300 µl of live bacteria containing 3 LD$_{50}$ of their respective bacterial strain. The bacterial suspension had been prepared from a broth culture in logarithmic phase growth, from which the bacteria was centrifuged, washed twice in PBS, and resuspended to the appropriate concentration in PBS. Animals were observed for a period of five days. Twenty-four to forty-eight hours post-challenge all animals in Group B (irrelevant antibody) and Group C (irrelevant organism) were dead. In contrast, those animals that had received the 4B9 (Group A) antibody were all alive and symptom free (Table 8).

TABLE 8

| Challenge Bacteria | Antibody | Survival/Challenge | % Survival |
|---|---|---|---|
| E. coli 025 | 4B9 | 10/10 | 100 |
| E. coli 025 | 6F11[a] | 0/10 | 0 |
| S. marcescens 014[b] | 4B9 | 0/10 | 0 |

[a] 6F11 antibody is specific to Pseudomonas aeruginosa Fisher immunotype 2 and serves as negative control antibody.
[b] S. marcescens 014 was not reactive with the antibody 4B9 and served as a nonspecific control organism.

For the group B streptococcus protection studies, a neonatal rat model was used. Outbred Sprague-Dawley rat pups (housed with their mothers), less than 48 hours old received antibody and bacteria essentially as described for the mouse protection studies. Primary differences were as follows: (1) both the antibodies and bacterial challenges were injected intraperitoneally, and (2) the inoculum size was reduced to 40 µl (Table 9).

TABLE 9

| Challenge Bacteria | Antibody | Survival/Challenge | % Survival |
|---|---|---|---|
| Group B strep, Type Ia | 4B9 | 10/10 | 100 |
| Type III | | 10/10 | 100 |
| Group B strep, Type Ia | 6F11[a] | 0/10 | 0 |
| Type III | | 0/10 | 0 |

[a] 6F11 antibody is specific to Pseudomonas aeruginosa Fisher immunotype 2 and serves as negative control antibody.

These data demonstrate that the human monoclonal antibody 4B9 is able to protect mice and rats from lethal challenges with bacteria genera belonging to both gram-negative and gram-positive bacterial divisions. The intergenus cross-reactive human monoclonal antibody 4B9 was able to afford protection with 25 µg of purified antibody against infection by organisms belonging to the gram-negative bacterium E. coli and the gram-positive group B streptococcus bacterium.

Using the procedures set forth in this Example, a second transformed cell line was produced which also secreted a human monoclonal antibody reactive with group B streptococci and E. coli. This monoclonal antibody, designated 3D2, was determined to bind the same antigen as recognized by antibody 4B9, was of the same isotype, exhibited similar in vitro characteristics, and protected animals prophylactically and therapeutically against challenge by homologous organisms. Using the methods and compositions of the present invention it would be within the ability of one skilled in the art to isolate additional cell lines which secrete monoclonal antibodies possessing characteristics similar to those described herein.

EXAMPLE III

Therapeutic Protection

As described in Examples I and II above, the monoclonal antibodies possessed the ability to protect animals against developing fatal infections when the antibodies were administered prophylactically and the animals subsequently challenged with lethal doses of organisms. Also of interest was whether the same monoclonal antibodies could cure animals in which infections by the homologous organism were already established. Antibodies 9B10 (anti-E. coli K1) and 4B9 (anti-group B streptococci) were used in therapeutic protection studies against infections caused by organisms within their respective genus. The antibodies were given to animals several hours after the injection of lethal amounts of organisms. Significantly, the monoclonal antibodies of the invention protected most animals from dying.

For the therapeutic protection studies, a neonatal rat model was used. Two to three day old outbred Spraque-Dawley (BK:SD) rat pups (housed with their dams) were injected intraperitoneally with 40 µl antibody 4 h or 8 h prior to an intraperitoneal challenge with 40 µl bacteria (5 LD$_{50}$'s).

To prepare the bacteria, broth culture tubes were inoculated from overnight stationary phase cultures of frozen maintained stock cultures. At logarithmic growth phase, the tubes were centrifuged at 22° C., 4550×g. for 10 min., washed once with 25 ml broth, and resuspended in same to the appropriate $OD_{660}$. For each experiment, dilutions of the bacterial source were plated on trypticase soy agar plates to quantitate the challenge dose, and on blood agar plates or other differential growth media to confirm culture purity. For the *E. coli* K1 experiments, neonatal rats were infected with 200–300 bacteria, and 4 or 8 hours later received 5.0 μg of purified antibody 9B10. For the group B streptococcal experiments neonatal rats were infected with 80–500 bacteria (varied among strains), and 4 s hours later received 20 μg of purified antibody 4B9. In all experiments, the pups were examined twice daily for symptoms, and scored for survival. A summary of the *E. coli* therapeutic protection studies is presented in Table 10.

TABLE 10

| Challenge Bacteria | Antibody | Hours Post-Infection[a] | Survival/Challenge | % Survival |
|---|---|---|---|---|
| *E. coli* K1 | 9B10 | 4 h | 13/13 | 100% |
| *E. coli* K1 | 9B10 | 8 h | 11/14 | 79% |
| *E. coli* K1 | 6F11[b] | 4 h | 0/12 | 0% |
| *E. coli* K1 | 6F11 | 8 h | 0/12 | 0% |
| group B streptococcus[c] | 9B10 | 4 h | 2/12 | 17% |

[a]Antibody administered 4 or 8 hours after infection.
[b]6F11 antibody is specific to *P. aeruginosa* Fisher immunotype 2 and served as a negative control antibody.
[c]Group B streptococci were not reactive with antibody 9B10 and served as nonspecific control organism.

A summary of the group B streptococcal therapeutic protection studies is presented in Table 11.

TABLE 11

| Challenge Bacteria | Antibody | Hours Post-Infection[a] | Survival/Challenge | % Survival |
|---|---|---|---|---|
| Group B streptococcus type Ia | 4B9 | 4 | 8/10 | 80% |
| Group B streptococcus type III | 4B9 | 4 | 9/10 | 90% |
| Group B streptococcus type Ia | 6F11[b] | 4 | 1/10 | 10% |
| Group B streptococcus type III | 6F11 | 4 | 3/10 | 30% |
| *E. coli* K1[c] | 4B9 | 4 | 0/10 | 0% |

[a]Antibody administered 4 or hours after infection.
[b]Negative control antibody.
[c]*E. coli* K1 are not reactive with antibody 9B10 and served as a nonspecific control organism.

These data demonstrate that the human monoclonal antibodies, 9B10 and 4B9, are able to therapeutically protect neonatal rats from lethal challenges with *E. coli* K1 and group B streptococci, respectively. Further it was shown that antibody 4B9 could provide cross-capsule serotype protection against the group B streptococci capsule serotypes Ia and III. The antigen specificity of the 4B9 antibody for group B streptococci was demonstrated to be the group B carbohydrate, a molecule common to all serotypes of group B streptococci.

From the foregoing, it will be appreciated that the cell lines of the present invention provide compositions of human monoclonal antibodies and fragments thereof cross-reactive for and cross-protective against various bacterial species, both gram-negative and gram-positive. This allows prophylactic and therapeutic compositions to be more easily developed that can be effective against nosocomial and neonatal infections due to most, if not all, bacterial genera. By combining the antibodies, it is possible to obtain broad protection against a large portion, usually less than all, of the clinically significant organisms. In addition, the cell lines provide antibodies which find uses in immunoassays and other well-known procedures.

Although the present invention has been described in some detail by way of illustration and example for purposes of clarity of understanding, it will be obvious that certain changes and modifications may be practiced within the scope of the appended claims.

What is claimed is:

1. A composition useful in the prophylactic or therapeutic treatment of bacterial infection due to group B streptococci, said composition comprising an in vivo protective monoclonal antibody or binding fragment thereof which binds to a group specific B carbohydrate epitope shared by serotypes of said group B streptococci.

2. A composition according to claim 1, wherein the monoclonal antibody is a human monoclonal antibody.

3. A composition according to claim 1, wherein the monoclonal antibody also binds with a gram-negative organism.

4. A composition according to claim 3, wherein the gram-negative organism is *Escherichia coli*.

5. A composition according to claim 4, wherein the *E. coli* is selected from the group consisting of serotypes 04, and 018.

6. A composition according to claim 3, wherein the gram-negative organism is *Serratia marcescens*.

7. A composition according to claim 1, wherein the binding of said monoclonal antibody to the group B streptococci is inhibited by rhamnose.

8. A composition according to claim 1, wherein the monoclonal antibody is an IgM isotype.

9. A composition comprising a monoclonal antibody or binding fragment thereof which binds to a group specific B carbohydrate epitope shared by serotypes of group B streptococci, wherein said antibody is bactericidal against said streptococci in the presence of active complement and neutrophils.

10. A composition comprising a monoclonal antibody or binding fragment thereof which binds to a group specific B carbohydrate epitope shared by serotypes of group B streptococci, wherein said antibody when administered to an animal which is subsequently challenged with a lethal amount of said streptococci, prevents the death of said animal.

11. The composition according to claim 10, wherein said antibody prevents the death of an animal due to an infection by group B streptococcus type Ia.

12. The composition according to claim 10, wherein said antibody prevents the death of an animal due to an infection by group B streptococcus type III.

13. A composition comprising a monoclonal antibody or binding fragment thereof which binds to a group specific B carbohydrate epitope shared by serotypes of group B streptococci, wherein said antibody, when administered to an animal infected with a lethal dose of said streptococci, prevents the death of said animal.

14. The composition according to claim 13, wherein said antibody prevents the death of an animal infected with at least about 5 LD$_{50}$ of said streptococci.

15. The composition according to claim 13, wherein said antibody prevents the death of an animal due to an infection by group B streptococci types Ia, II or III.

16. A composition according to claim 13, wherein said antibody is useful in treating infections due to multiple serotypes of said group B streptococci.

17. A composition according to any of claims 1, 9, 10 or 13, wherein said monoclonal antibody is lyophilized.

18. A pharmaceutical composition according to any of claims 1, 9, 10 or 13, further comprising a physiologically acceptable carrier.

19. A pharmaceutical composition according to any of claims 1, 9, 10 or 13, further comprising an antimicrobial agent.

20. A pharmaceutical composition according to any of claims 1, 9, 10, or 13, further comprising a gamma globulin fraction from human blood plasma.

21. An immortal cell line which secretes a human monoclonal antibody or binding fragment thereof which binds to an epitope of the group specific B carbohydrate shared by serotypes of group B streptococci, wherein said human monoclonal antibody is protective in vivo against infection by said group B streptococci.

22. The cell line according to claim 21, wherein the monoclonal antibody also binds with a lipopolysaccharide epitope of a gram-negative bacterium.

23. The cell line according to claim 22, wherein the gram-negative bacterium is *E. coli*.

24. The immortal cell line ATCC No. CRL 9008 or a subclone thereof.

25. A human monoclonal antibody or binding fragment thereof produced by the cell line of claim 24 or a subclone thereof and which is protective in vivo against infection by group B streptococci.

26. A human monoclonal antibody or a binding fragment thereof obtained from the cell line of claim 24 or a subclone thereof.

27. The human monoclonal antibody of claim 26, which antibody is conjugated to a label.

28. A method of treating a patient to prevent an infection due to group B streptococci, said method comprising administering a prophylactically effective amount of a composition according to any of claims 1, 9, 10 or 13.

29. A method according to claim 28, wherein said composition is administered intravenously.

30. A method of treating a patient infected with group B streptococci, said method comprising administering a therapeutically effective amount of a composition according to any of claims 1, 9, 10 or 13.

31. A method of treating a patient according to claim 30, wherein said composition is administered intravenously.

32. A method for treating a patient for an infection by group B streptococci, said method comprising administering a therapeutically or prophylactically effective amount of a composition which comprises an in vivo protective monoclonal antibody or binding fragment thereof which binds to a group specific B carbohydrate epitope shared by serotypes of said group B streptococci.

33. The method according to claim 32, wherein said monoclonal antibody is human.

34. The method according to claim 33, wherein said monoclonal antibody protects therapeutically against infection caused by group B streptococcus type Ia.

35. The method according to claim 33, wherein said monoclonal antibody protects therapeutically against infection caused by group B streptococcus type II.

36. The method according to claim 33, wherein said monoclonal antibody protects therapeutically against infection caused by group B streptococcus type III.

37. The method according to claim 32, wherein the monoclonal antibody or a binding fragment thereof is obtained from cell line ATCC CRL 9008 or a subclone thereof.

38. The method according to claim 32, wherein the binding of said monoclonal antibody to group B streptococci is inhibited by rhamnose.

39. The method according to claim 32, wherein said monoclonal antibody is an IgM.

40. The method according to claim 32, wherein said composition is administered intravenously.

41. The method according to claim 32, wherein the monoclonal antibody also binds with a lipopolysaccharide epitope of *E. coli*.

42. The method according to claim 41, wherein the *E. coli* is serotype 04 or 018.

* * * * *